(12) United States Patent
Huskey et al.

(10) Patent No.: US 6,727,244 B2
(45) Date of Patent: Apr. 27, 2004

(54) MAMMALIAN METABOLITES OF A TACHYKININ RECEPTOR ANTAGONIST

(75) Inventors: Su-er Wu Huskey, Westfield, NJ (US); Shuet-Hing Lee Chiu, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/415,205

(22) PCT Filed: Oct. 23, 2001

(86) PCT No.: PCT/US01/46229
§ 371 (c)(1),
(2), (4) Date: Apr. 24, 2003

(87) PCT Pub. No.: WO02/34699
PCT Pub. Date: May 2, 2002

(65) Prior Publication Data
US 2004/0023960 A1 Feb. 5, 2004

Related U.S. Application Data

(60) Provisional application No. 60/243,518, filed on Oct. 26, 2000.

(51) Int. Cl.$^7$ .............. A61K 31/5375; A61P 25/24; C07D 265/32
(52) U.S. Cl. .............. 514/230.8; 514/228.8; 544/98; 544/174
(58) Field of Search .............. 544/98, 174; 514/230.8

(56) References Cited

U.S. PATENT DOCUMENTS 5,719,147 A * 2/1998 Dorn et al. .............. 514/225.5
6,096,742 A * 8/2000 Crocker et al. .............. 544/132

* cited by examiner

*Primary Examiner*—Robert Ramsuer
(74) *Attorney, Agent, or Firm*—J. Eric Thies; Melvin Winokur

(57) ABSTRACT

This invention is concerned with mammalian metabolites of the compound 2-(R)-(1-(R)-(3,5-bis(trifluoromethyl)phenyl)ethoxy)-3-(S)-(4-fluoro)-phenyl-4-(3-(5-oxo-1H,4H-1,2,4-triazolo)methylmorpholine which is a tachykinin receptor antagonist that is useful in the prevention and treatment of certain disorders, including emesis and psychiatric disorders such as depression and anxiety.

6 Claims, No Drawings

MAMMALIAN METABOLITES OF A TACHYKININ RECEPTOR ANTAGONIST

CROSS REFERENCE TO RELATED APPLICATIONS

This application is a U.S. National Phase application under 35 U.S.C. §371 of PCT Application No. PCT/US01/46229, filed Oct. 23, 2001, which claims priority under 35 U.S.C. §119 from Provisional Application No. 60/243,518, filed Oct. 26, 2000.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to SP the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Evidence has been reviewed for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia.

It has furthermore been suggested that tachykinin receptor antagonists have utility in the following disorders: anxiety, depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus, ophthalmic diseases such as conjunctivitis, vernal conjunctivitis, and the like, and cutaneous diseases such as contact dermatitis, atopic dermatitis, urticaria, and other eczematoid dermatitis.

Attempts have been made to provide antagonists for the receptors of substance P and other tachykinin peptides in order to more effectively treat the various disorders and diseases. In particular, U.S. Pat. No. 5,719,147, Example 75, and U.S. Pat. No. 6,096,742 disclose the compound 2-(R)-(1-(R)-(3,5-bis(trifluoro-methyl)-phenyl)ethoxy)-3-(S)-(4-fluoro)phenyl-4-(3-(5-oxo-1H,4H-1,2,4-triazolo)-methylmorpholine which has the structure:

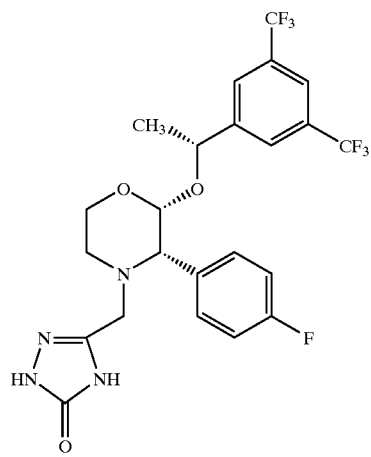

U.S. Pat. No. 5,719,147, Example 75 and U.S. Pat. No. 6,096,742 disclose methods for preparing this compound.

SUMMARY OF THE INVENTION

The present invention is directed to mammalian metabolites of the compound 2-(R)-(1-(R)-(3,5-bis(trifluoromethyl)-phenyl)ethoxy)-3-(S)-(4-fluoro)-phenyl-4-(3-(5-oxo-1H,4H-1,2,4-triazolo)methylmorpholine and the process for the preparation of these compounds.

The present invention is also concerned with pharmaceutical formulations comprising these mammalian metabolites as an active ingredient and the use of these compounds and their formulations in the treatment of certain disorders and diseases.

The mammalian metabolites of this invention are tachykinin receptor antagonists useful in the treatment or prevention of inflammatory diseases, emesis, depresssion, anxiety, and other neuropsychiatric diseases, including bipolar disorder and schizophrenia.

DESCRIPTION OF THE INVENTION

The present invention is directed to mammalian metabolites of the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine and processes for the preparation of these compounds.

The compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine has the structure:

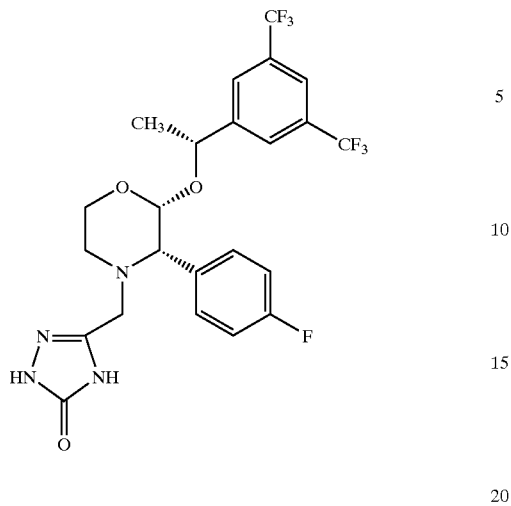

and is a tachykinin receptor antagonist useful in the treatment of inflammatory diseases, emesis, depresssion, anxiety, and other neuropsychiatric diseases, including bipolar disorder and schizophrenia.

The compounds of the present invention are mammalian metabolites of the compound 2-(R)-(1-(R)-(3,5-bis(trifluoromethyl)-phenyl)ethoxy)-3-(S)-(4fluoro)-phenyl-4-3-(5-oxo-1H,4H-1,2,4-triazolo)methylmorpholine.

The present invention is directed to a compound which is selected from the group consisting of:

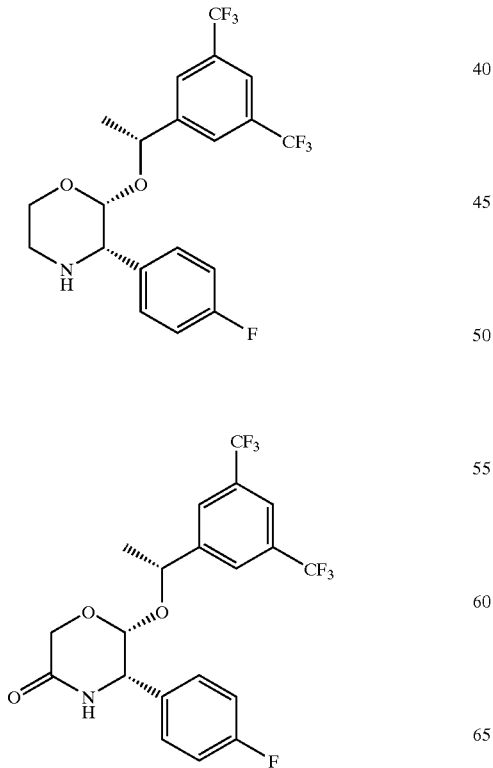

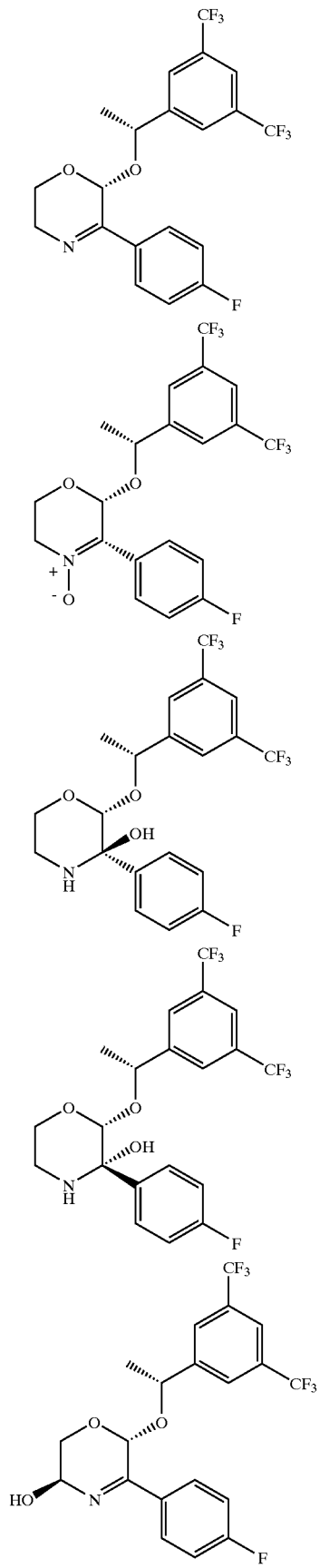

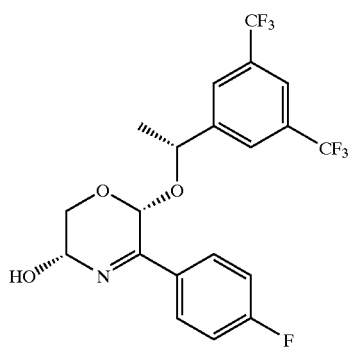
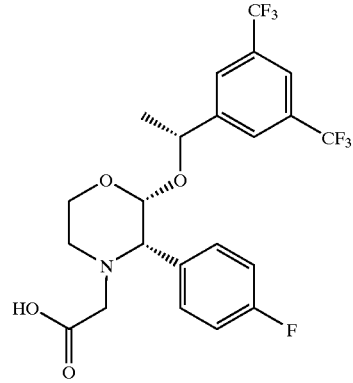
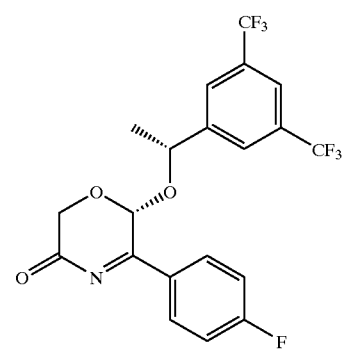
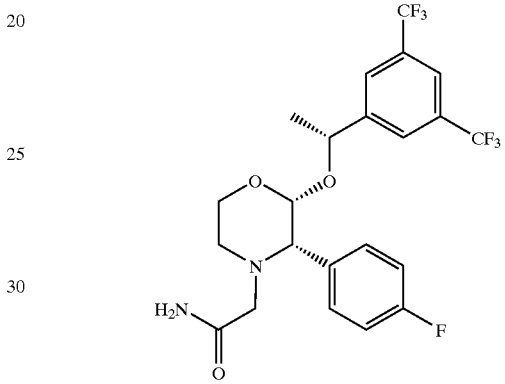
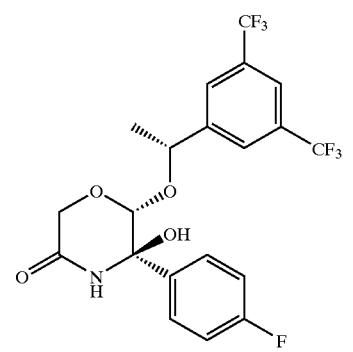
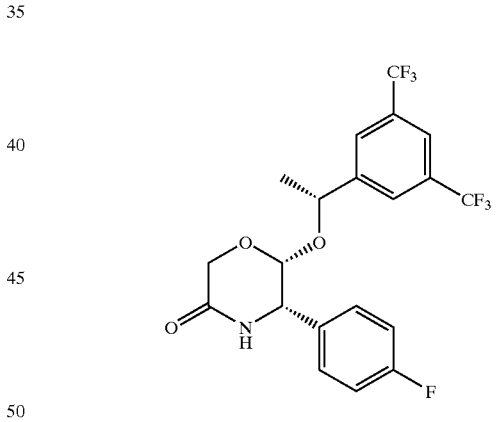
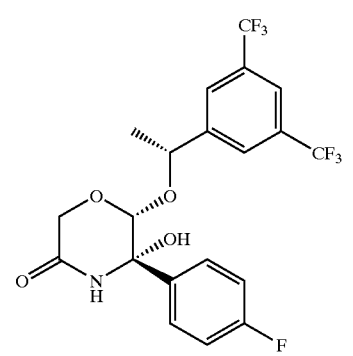
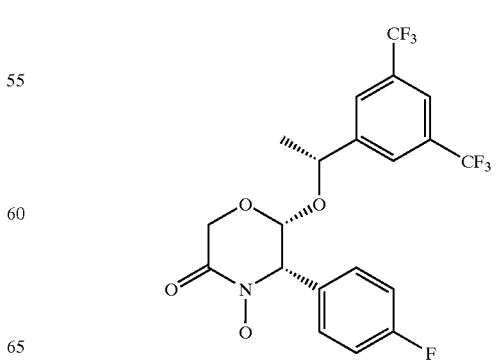

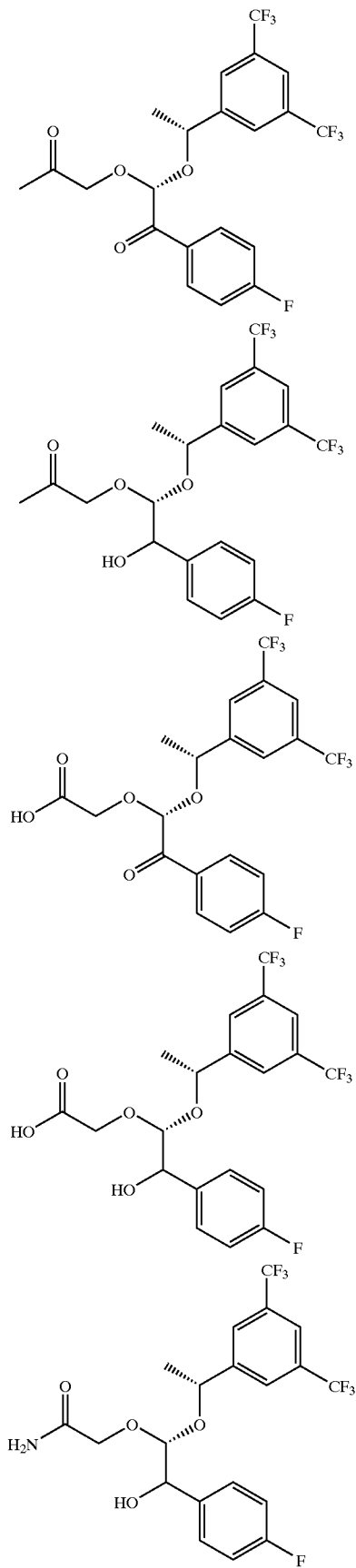

-continued

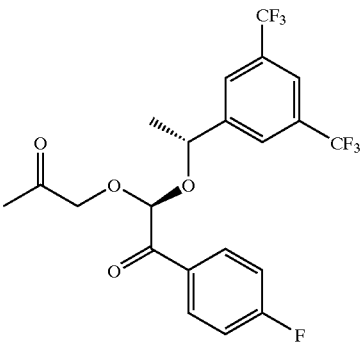

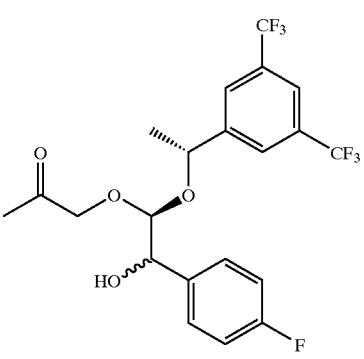

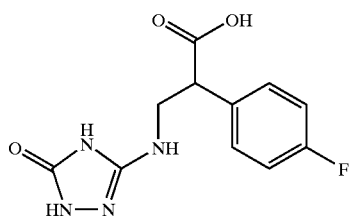

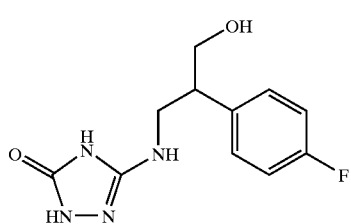

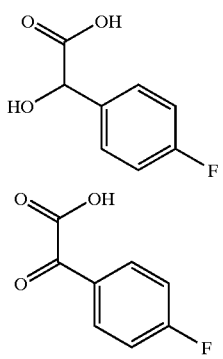

-continued

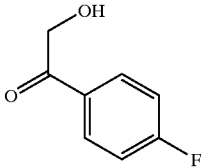

and pharmaceutically acceptable salts and individual diasteromers thereof.

These compounds are among the mammalian metabolites of 2-(R)-(1-(R)-(3,5-bis(trifluoromethy)phenyl)ethoxy)-3-(S)-(4-fluoro)phenyl-4-(3-(5-oxo-1H,4H-1,2,4-triazolo) methylmorpholine.

The parent compound and some of these mammalian metabolites may be named alternatively as follows:

Parent Compound: 5-[[(2R,3S)-2-[(1R)-1-[3,5-bis (trifluoromethyl)phenyl]ethoxy]-3-(4-fluorophenyl)4-morpholinyl]methyl]-1,2-dihydro-3H-1,2,4-triazol-3-one;

M-1: (2R,3S)-2-[(1R)-1-[3,5-bis(trifluoromethyl)phenyl] ethoxy]-3-(4-fluorophenyl)morpholine;

M-2: (2R)-2-[(1R)-1-[3,5-bis(trifluoromethyl)phenyl] ethoxy]-3-(4-fluorophenyl)-5,6-dihydro-2H-1,4-oxazine;

M-3: (5S,6R)-6-[(1R)-1-[3,5-bis(trifluoromethyl)phenyl] ethoxy]-5-(4-fluorophenyl)-3-morpholinone;

M4: (6R)-6-[(1R)-1-[3,5-bis(trifluoromethyl)phenyl] ethoxy]-5-(4-fluorophenyl)-5-hydroxy-3-morpholinone;

M-5: [(1R)-1-[(1R)-1-[3,5-bis(trifluoromethyl)phenyl] ethoxy]-2-(4-fluorophenyl)-2-oxoethoxy]acetic acid;

M-6: [(1R)-1-[(1R)-1-[3,5-bis(trifluoromethyl)phenyl] ethoxy]-2-(4-fluorophenyl)-2-hydroxyethoxy]acetic acid.

The present invention is also concerned with a process for the preparation of the mammalian metabolites of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo) methylmorpholine which comprises:

administering 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine to a mammal, such as a human. Optionally, the mammalian metabolites may be isolated from the urine or feces.

Preferably, the parent compound 2-(R)-(1-(R)-(3,5-bis (trifluoromethyl)phenyl)ethoxy)-3-(S)-(4-fluoro)phenyl-4-(3-(5-oxo-1H,4H-1,2,4-triazolo)methylmorpholine is administered to the mammal orally.

The present invention is directed to the mammalian metabolites as they are formed in vivo upon administration of the parent compound 2-(R)-(1-(R)-(3,5-bis (trifluoromethyl)-phenyl)ethoxyl)-3-(S)-(4-fluoro)phenyl-4-(3-(5-oxo-1H,4H-1,2,4-triazolo)methylmorpholine to a mammalian species such as a human, as well as such mammalian metabolites as pure or partially purified compounds.

The specific pathways responsible for the mammalian metabolism of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine to some of the subject metabolites may be summarized as follows:

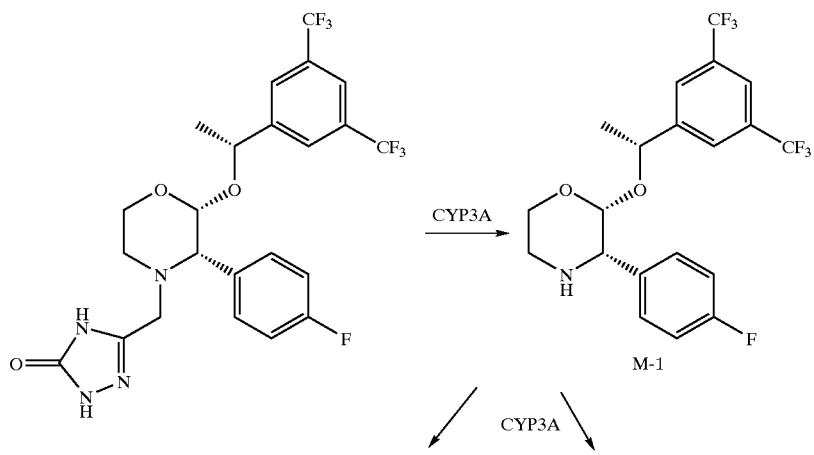
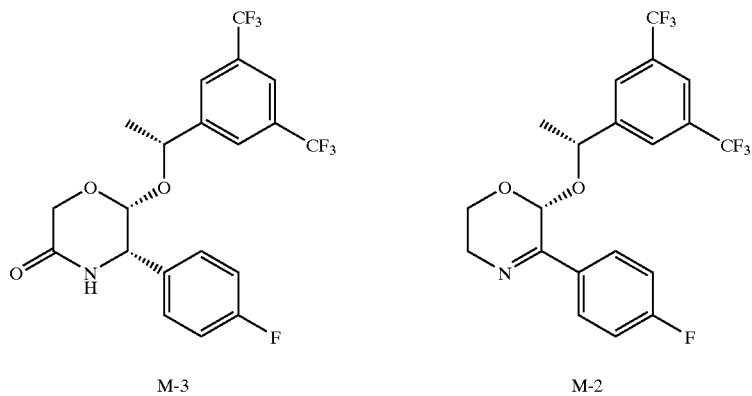
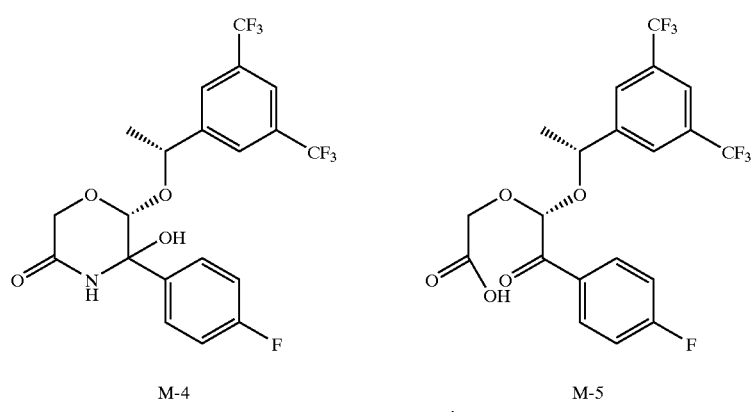

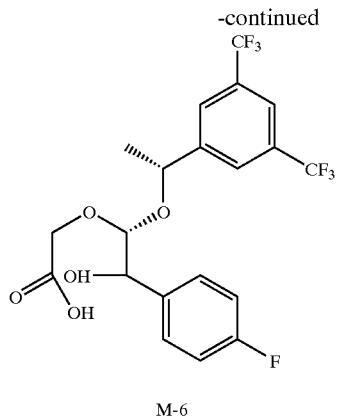

M-6

The primary metabolite (M-1) of 2-(R)-(1-(R)-(3,5-bis (trifluoro-methyl)-phenyl)ethoxy)-3-(S)-(4-fluoro)phenyl-4-(3-(5-oxo-1H,4H-1,2,4-triazolo)methylmorpholine is the N-dealkylated derivative. The N-dealkylated metabolite (M-1) is present in incubates with liver microsomes from rats, dogs and humans. When (M-1) is incubated in the primary rat hepatocyte culture, several metabolites are obtained including the imine derivative of morpholine (M-2), the lactam derivative of morpholine (M-3), the hydroxy lactam (M-4), the morpholine-ring opened ketocarboxylic acid (M-5) and the corresponding hydroxycarboxylic acid (M-6). These metabolites result from at least 6 metabolic events on 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine: N-dealkylation to the destriazolone derivative (M-1), oxidation at the benzylic carbon on the morpholine ring to form the imine derivative (M-2), oxidation alpha to the morpholine nitrogen to form a lactam (M-3), oxidation of the lactam to form a hydroxylated lactam (M-4), morpholine ring-opening followed by hydrolysis to the corresponding keto carboxylic acid (M-5), and reduction of the keto carboxylic acid to the hydroxy carboxylic acid (M-6). Consistent with the results of the in vitro studies, these metabolites (M-1 to M-6) also were found in the plasma of rats, dogs and humans following administration of 2-(R)-(1-(R)-(3,5-bis(trifluoro-methyl)-phenyl)ethoxy)-3-(S)-(4-fluoro)phenyl-4-(3-(5-oxo-1H,4H-1,2,4-triazolo)-methylmorpholine.

Using microsomes containing recombinant human CYP isozymes, CYP3A4 is being primarily responsible for the N-dealkylation of the parent compound to M-1; for the subsequent oxidation of M-1 to M-2; and for the hydroxylation of M-3 to from M-4 and the conversion of M-2 to M-5.

The primary metabolite (M-1) of 2-(R)-(1-(R)-(3,5-bis (trifluoro-methyl)-phenyl)ethoxy)-3-(S)-(4-fluoro)phenyl-4-(3-(5-oxo-1H,4H-1,2,4-triazolo)methylmorpholine is the N-dealkylated derivative had an $IC_{50}$ value for human $NK_1$ receptor binding activity of 1 nM. In vitro metabolism of (M-1) was examined using liver microsomes from humans and a major metabolite (M-2) was identified as the imine derivative of (M-1). The $IC_{50}$ value for human $NK_1$ receptor binding activity of (M-2) was ~10 nM.

Two metabolites present in brain homogenates are as isomeric hydroxylated lactam derivatives (M-4). The mixture had an $IC_{50}$ value of 28 nM for the human $NK_1$ receptor. One of these metabolites also is present in the plasma and liver tissue of rats dosed with the parent compound.

Using primary rat hepatocyte cultures, a lactam derivative (M-3) and the imine metabolite (M-2) are major metabolites after incubation of the parent compound at 37° C. for 6 hr. (M-3) had an $IC_{50}$ value of 4 nM for the human $NK_1$ receptor. Several metabolites derived from morpholine ring-opening were identified, including (M-5) and (M-6). Among these acid metabolites, (M-6) had an $IC_{50}$ value of 18 nM in the human $NK_1$ receptor binding assay.

The present invention is further concerned with an alternate process for the preparation of the mammalian metabolites of 2-(R)-(1-(R)-(3,5-bis(trifluoro-methyl)-phenyl) ethoxy)-3-(S)-(4-fluoro)phenyl-4-(3-(5-oxo-1H,4H-1,2,4-triazolo)-methylmorpholine which comprises:

incubating a mixture of 2-(R)-(1-(R)-(3,5-bis (trifluoromethyl)-phenyl)ethoxy)-3-(S)-(4-fluoro) phenyl-4-(3-(5-oxo-1H,4H-1,2,4-triazolo)-methylmorpholine and mammalian liver microsomes.

Preferably, the compound 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)-methylmorpholine is incubated in the presence of $MgCl_2$ and NADPH in a buffer of approximately neutral pH at a temperature of approximately 30–40° C.

The desired-metabolites may be isolated from the biological matrix by methods well known in the art, such as via selective solid phase or solvent extraction and purification by liquid chromatography (LC) or high performance liquid chromatography (HPLC) using different stationary phase and mobile phase conditions. These procedures and the results of the experiments are noted in the Examples.

The present metabolites may also be formed in vivo upon administration of the parent compound 2-(R)-(1-(R)-(3,5-bis(trifluoromethyl)-phenyl)ethoxy)-3-(S)-(4-fluoro) phenyl-4-(3-(5-oxo-1H,4H-1,2,4-triazolo)methyl-morpholine to a mammalian species, such as a human.

The parent compound 2-(R)-(1-(R)-(3,5-bis (trifluoromethyl) -phenyl)ethoxy)-3-(S)-(4-fluoro)phenyl-4-(3-(5-oxo-1H,4H-1,2,4-triazolo)methyl-morpholine may be prepared as described in Example 75 of U.S. Pat. No. 5,719,147 and U.S. Pat. No. 6,096,742.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

In addition compounds with carbon-carbon double bonds may occur in Z- and E- forms with all isomeric forms of the compounds being included in the present invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of the compounds disclosed herein; and pharmaceutically acceptable salts thereof and individual diastereomers thereof.

Throughout the instant application, the following abbreviations are used with the following meanings:

Reagents:

| | |
|---|---|
| Cbz-Cl | benzyl chloroformate |
| BOP | benzotriazol-1-yloxy tris(dimethylamino)phosphonium hexafluorophosphate |
| CDI | 1,1'-carbonyldiimidazole |
| ACE-Cl | alpha-chloroethyl chloroformate |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DIBAL | diisobutylaluminum hydride |
| iPr$_2$NEt or DIPEA | N,N-diisopropylethylamine |
| EDC | 1-(3-dimethylaminopropyl)-3-ethylcarbodiimide hydrochloride |
| DMAP | 4-dimethylaminopyridine |
| Me$_2$SO$_4$ | dimethyl sulfate |
| EDAC | 1-ethyl-3-(3-dimethylaminopropyl)carbodiimide hydrochloride |
| HOBt | 1-hydroxybenzotriazole hydrate |
| NHS | N-hydroxysuccinimide |
| LAH | lithium aluminum hydride |

| | |
|---|---|
| LHMDS | lithium bis(trimethylsilyl)amide |
| NMM | N-methylmorpholine |
| KHMDS | potassium bis(trimethylsilyl)amide |
| NaOEt | sodium ethoxide |
| Et$_3$N | triethylamine |
| Ph$_3$P | triphenylphosphine |
| TFA | trifluoroacetic acid |

Solvents:

| | |
|---|---|
| AcOH | acetic acid |
| MeCN | acetonitrile |
| AmOH | n-amyl alcohol |
| DMSO | dimethylsulfoxide |
| DMF | N,N-dimethylformamide |
| EtOH | ethanol |
| MeOH | methanol |
| THF | tetrahydrofuran |

Others:

| | |
|---|---|
| Am | n-amyl |
| Ar | aryl |
| BOC | tert-butoxycarbonyl |
| Bn | benzyl |
| Bu | butyl |
| Cbz | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| H or hr | hour(s) |
| HPLC | high pressure liquid chromatography |
| iPr | isopropyl |
| MPLC | medium pressure liquid chromatography |
| Me | methyl |
| MHz | megahertz |
| Min | minute(s) |
| MF | molecular formula |
| NMR | nuclear magnetic resonance |
| Ph | phenyl |
| PTC | phase transfer catalyst |
| prep. | prepared or preparative |
| Pr | propyl |
| rt | room temperature |
| TLC | thin layer chromatography |
| TMS | tetramethylsilane |

The preparation of compounds of Formula I of the present invention may be carried out by metabolic processes or in sequential or convergent synthetic routes. Metabolic processes and chemical syntheses detailing the preparation of the compounds of the present invention in a sequential manner are presented in the following examples. The skills required in carrying out the reaction and purification of the resulting reaction products are known to those in the art. Purification procedures includes crystallization, normal phase or reverse phase chromatography.

Several methods for preparing the compounds of this invention are illustrated in the following Examples.

It is noted that in some cases the order of carrying out the foregoing reaction steps may be varied to facilitate the reaction or to avoid unwanted reaction products.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZA-PPER (IBI). The transfected cells were incubated in CHO media [10 % fetal calf serum, 100 U/ml pennicilin-streptomycin, 2 mM glutamine, 1/500 hypoxanthine-thymidine (ATCC), 90% IMDM media (JRH BIOSClENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1 % polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0:1 N formic acid followed by 0.025 M ammonium formate-0.1 N formic acid. The inositol monophosphate is eluted with 0.2 M ammonium formate-0.1 N formic acid and quantitated by beta counter.

In particular, the intrinsic tachykinin receptor antagonist activities of the compounds of the present invention may be demonstrated by this assay. Many of the compounds of the present invention have activity in the aforementioned assay at a level of less than about 10 $\mu$M. The activity of the present compounds may also be demonstrated by the assay disclosed by Lei, et al., *British J. Pharmacol.*, 105, 261–262 (1992).

With respect to the use of the parent compound 2-(R)-(1-(R)-(3,5-bis(trifluoromethyl -phenyl)ethoxy)-3-(S)-(4-fluoro)phenyl-4-(3-(5-oxo-1H,4H-1,2,4-triazolo) methylmorpholine disclosed in U.S. Pat. No. 5,719,147, Example 75, and U.S. Pat. No. 6,096,742, the present mammalian metabolites exhibit unexpected properties, such as with respect to improved side effect profile, CNS-penetrancy, aqueous solubility, duration of action and/or metabolism, such as enhanced oral bioavailability or absorption.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extrapyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of the present invention are also of value in the treatment of a combination of the above conditions, in particular in the treatment of combined post-operative pain and post-operative nausea and vomiting.

The compounds of the present invention are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of the present invention are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of the present invention are also of use in the treatment of emesis induced by radiation including radiation therapy such as in the treatment of cancer; and in the treatment of post-operative nausea and vomiting.

It will be appreciated that the compounds of the present invention may be presented together with another therapeutic agent as a combined preparation for simultaneous, separate or sequential use for the relief of emesis. Such combined preparations may be, for example, in the form of a twin pack.

A further aspect of the present invention comprises the compounds of the present invention in combination with a 5-HT$_3$ antagonist, such as ondansetron, granisetron or tropisetron, or other anti-emetic medicaments, for example, a dopamine antagonist such as metoclopramide or domperidone or GABAB receptor agonists such as baclofen. Additionally, a compound of the present invention, either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of the present invention may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of the present invention are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The compounds of the present invention are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; bipolar disorders or manic depression, for example, bipolar I disorder, bipolar II disorder and cyclothymic disorder.

The present invention further provides a compound of the present invention for use in therapy.

According to a further or alternative aspect, the present invention provides a compound of the present invention for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The present invention is further directed to a method for the manufacture of a medicament for antagonizing the effect of substance P or another tachykinin at its receptor site or for the blockade of neurokinin-1 receptors or other tachykin receptors in a mammal comprising combining a compound of the present invention with a pharmaceutical carrier or diluent.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a further aspect of the present invention, it may be desirable to treat any of the aforementioned conditions with a combination of a compound according to the present invention and one or more other pharmacologically active agents suitable for the treatment of the specific condition. The compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above.

Also, for the treatment of respiratory diseases, such as asthma, a compound of the present invention may be used in conjunction with a bronchodilator, such as a $\beta_2$-adrenergic receptor agonist or a tachykinin antagonist which acts at neurokinin-2 receptors. Suitable $\beta_2$-adrenergic receptor agonist include: Bambuterol (U.S. Pat. No. 4,419,364 issued to Draco on Dec. 6, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 21, 1973); Clenbuterol (U.S. Pat. No. 3,536,712 issued to Boehringer Ingelheim Oct. 27, 1970); Cimaterol (U.S. Pat. No. 4,407,819 issued to American Cyanamid Oct. 4,1983); Docarpamine (U.S. Pat. No. 4,228,183 issued to Tanabe Oct. 14, 1980); Dopexamine (U.S. Pat. No. 4,645, 768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. Pat. No. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exempified by those disclosed in Patent Pub. EP 0,480,717, published Apr. 15, 1992; Patent Pub. EP 0604,114, published June 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in conjunction with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

The present invention accordingly provides a method for the treatment of a respiratory disease, such as asthma, which method comprises administration to a patient in need thereof of an effective amount of a compound of the present invention and an effective amount of a bronchodilator.

The present invention also provides a composition comprising a compound of the present invention, a bronchodilator, and a pharmaceutically acceptable carrier.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

It will be appreciated that for the treatment or prevention of migraine, a compound of the present invention may be used in conjunction with other anti-migraine agents, such as ergotamines or $5-HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of the present invention, a bronchodilator, and a pharmaceutically acceptable carrier.

It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, a-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable $5\text{-HT}_{1A}$ receptor agonists or antagonists include, in particular, the $5\text{-HT}_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of the present invention and an anorectic agent for the manufacture of a medicament for the treatment or prevention of eating disorders.

The present invention also provides a method for the treatment or prevention of eating disorders, which method comprises administration to a patient in need of such treatment an amount of a compound of the present invention and an amount of an anorectic agent, such that together they give effective relief.

In a further aspect of the present invention, there is provided a pharmaceutical composition comprising a compound of the present invention and an anorectic agent, together with at least one pharmaceutically acceptable carrier or excipient.

It will be appreciated that the compound of the present invention and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of the present invention and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of the present invention and an SSRI for the manufacture of a medicament for the treatment or prevention of obesity.

The present invention also provides a method for the treatment or prevention of obesity, which method comprises administration to a patient in need of such treatment an amount of a compound of the present invention and an amount of an SSRI, such that together they give effective relief.

In a further aspect of the present invention, there is provided a pharmaceutical composition for the treatment or prevention of obesity comprising a compound of the present invention and an SSRI, together with at least one pharmaceutically acceptable carrier or excipient.

It will be appreciated that the compound of the present invention and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of the present invention and an SSRI as a combined preparation for simultaneous, separate or sequential use in the treatment or prevention of obesity.

Suitable selective serotonin reuptake inhibitors of use in combination With a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention further relates to the use of a compound of the present invention for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of the present invention or a pharmaceutically acceptable salt thereof.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

The following examples are provided for the purpose of further illustration only and are not intended to be limitations on the disclosed invention.

EXAMPLE 1

(2-R)-2-((R)-1-(3,5-Bis(trifluoromethyl)phenyl)ethoxy)-2-(methoxycarbonyl-methoxy)-4'-fluoroacetophenone (higher $R_f$ diastereomer) and (2-S)-2-((R)-1-(3,5-bis(trifluoromethyl)phenyl)ethoxy)-2-(methoxycarbonylmethoxy)4'-fluoro-acetophenone (lower $R_f$ diastereomer)

Method A

Step A: (R)-1-(3,5-Bis(trifluoromethyl)phenyl)ethanol

A solution of 530 mg of (S)-(−)-α,α-diphenyl-2-pyrrolidinemethanol in 35 mL of THF was cooled to −10° C. in an ice/ethanol bath. A 1.0 M solution of borane-THF was added dropwise while maintaining the temperature below −5° C. The ice bath was then removed and the reaction was stirred at room temperature for 3.5 h. To this solution was added dropwise at room temperature over 20 min 5.0 g of 3',5'-bis(trifluoromethyl)acetophenone in 10 mL of THF. After stirring a further 20 min, the reaction was quenched by pouring into a mixture of 20 mL of 12 N HCl in 100 g of ice water. The mixture was stirred at room temperature for 16 h and then diluted with 400 mL of 1:1 ether:ethyl acetate and the layers were separated. The organic layer was washed with 1.2 N HCl and brine, dried over magnesium sulfate, filtered and evaporated. The residue was taken up in 200 mL of hexanes and cooled in a dry ice/acetone bath to precipitate 4.28 g of title compound as a white solid after filtration and drying. $[\alpha]_D$ (CHCl$_3$)=+22.9 (c=1.2) (lit., J. Am. Chem. Soc., 1990, 112, 5741, $[\alpha]_D$ (CHCl$_3$)=+21.0 (c=1.0)). NMR (CDCl$_3$): δ1.54 (d, 3 H, J=6.5 Hz), 5.04 (q, 1 H, J=6.5 Hz), 7.77 (s, 1 H), 7.82 (s, 2 H).

Step B: 4-Fluorophenylglyoxal hydrate

The title compound was prepared using essentially the same procedure as described by H. A. Riley and A. R. Gray in Organic Synthesis, Collective Volume II, p. 509 for the preparation of phenylglyoxal hydrate, but using 4'-fluoroacetophenone in place of acetophenone.

Thus, 18.5 g of selenium dioxide was dissolved in 100 mL of dioxane by warming to 50° C. and stirring until all was in solution. To this solution was added. 23 g of 4'-fluoroacetophenone and the reaction was refluxed for 4 h. The hot solution was decanted from the solid selenium and the dioxane and water were removed by distillation through a short column at atmospheric pressure. Distillation of the residue at reduced pressure afforded 20 g of 4-fluorophenylglyoxal as a thick yellow oil which was contaminated by some starting 4'-fluoroacetophenone. This can be used directly or, more preferably, it can be converted to pure hydrate (see the last paragraph of the reference and note 5). A portion was boiled in water for 0.5 h and the aqueous layer was decanted from an oily residue and then allowed to cool. The hydrate is obtained as a white solid after filtration and air drying.

Step C: (2-R)-2-((R)-1-(3,5-Bis(trifluoromenthyl)phenyl)-ethoxy)-2-(methoxycarbonylmethoxy)-4'-fluoroacetophenone (higher $R_f$ diastereomer) and (2-S)-2-((R)-1-(3,5-bis(trifluoromethyl)phenyl)-ethoxyl)-2-(methoxycarbonylmethoxy)-4'-fluoroacetophenone (lower $R_f$ diastereomer)

A suspension of 1.25 g of (R)-1-(3,5-bis(trifluoromethyl)phenyl)-ethanol from Step A, 0.665 g of 4-fluorophenylglyoxal hydrate from Step B, 1.05 g of fresh methyl glycolate and 2 g of 4A sieves in 10 mL of methylene chloride was warmed to 50° C. and then stirred at room temperature for 16 h (to remove water). The sieves were removed by filtration and the filtrate was placed under nitrogen and cooled in an ice bath. To this solution was added 0.70 mL of trimethylsilyl trifluoromethylsulfonate and the reaction was stirred at 0° C. for 4 h. The reaction was then quenched by slow addition to a stirred mixture of sat'd sodium bicarbonate solution and ether. The layers were separated and the aqueous layer was reextracted with ether. The organic layers were each washed with brine, dried over sodium sulfate, combined and evaporated. Careful FC of the residue (0 to 25% ethyl acetate in hexanes) gave several products in the following order: (R)-1-(3,5-bis(trifluoro-methyl)phenyl)phenyl)ethyl ether, 2,2-di-((R)-1-(3,5-bis(trifluoromethyl)phenyl)-ethoxy)4'-fluoroacetophenone, (2-R and 2-S)-2-((R)-1-(3,5-bis(trifluoromethyl)phenyl)ethoxy)-2-(methoxy)4'-fluoroacetophenone, the desired (2-R) title compound (2–5%), starting (R)-1-(3,5-bis(trifluoromethyl)phenyl)ethanol, the diastereomeric (2-S) title compound (2–5%), (2-R and 2-S)-2-(methoxy)-2-(methoxycarbonylmethoxy)-4'-fluoroacetophenone and 1,1-di-(methoxycarbonylmethoxy)-4'-fluoroacetophenone.

(Higher $R_f$ (2-R) title product: NMR (CDCl$_3$): δ1.56 (d, 3 H, J=6.5 Hz), 3.72 (s, 3 H), 4.10 and 4.25 (ABq, 2 H, J=6.6 Hz), 5.16 (s, 1 H), 5.28 (q, 1 H, J=6.5 Hz), 7.08 (m, 2 H), 7.77 (s, 2 H), 7.78 (s, 1 H), 8.08 (m, 2 H).

(Lower $R_f$ (2-S) title product:
NMR (CDCl$_3$): δ1.51 (d, 3 H, J=6.5 Hz), 3.66 (s, 3 H), 4.10 and 4.15 (ABq, 2 H, J=17 Hz), 5.12 (q, 1 H, J=6.5 Hz), 5.46 (s, 1H), 7.08 (m, 2 H), 7.77 (s, 2 H), 7.78 (s, 1H), 8.08 (m, 2 H).

Method B
Step A: 2,2-Di-((R)-1-(3,5-bis(trifluoromethyl)phenyl) ethoxyl)4'-fluoroacetophenone
Method AA A 100-mL round-bottomed flask equipped with a nitrogen inlet adapter and magnetic stir bar was charged with 0.664 g of 4-fluorophenylglyoxal hydrate from Method A, Step B, 0.5 gm of 4A molecular sieves, and 40 mL of dry methylene chloride and stirred at room temperature. After 3 h, 2.52 g of (R)-1-(3,5-bis(trifluoromethyl)phenyl)ethanol from Method A, Step A, was added and the solution was stirred for an additional 3.5 h. The resulting solution was then quickly filtered through celite and placed under nitrogen. To this solution was added 0.710 ml of trimethylsilyl trifluoromethanesulfonate at room temperature. The reaction mixture turned orange in color and after 12 h the reaction mixture was diluted with 40 mL of methylene chloride and poured into 100 mL of saturated sodium bicarbonate solution. The phases were separated, and the aqueous phase was extracted with two 40 mL portions of methylene chloride. The combined organic phases were washed with brine, dried over sodium sulfate, filtered and concentrated. FC on silica gel (gradient elution with 5–40% ethyl acetate / hexanes) afforded 1.2 g (51%) of title compound as an oil.

NMR (CDCl$_3$): δ8.04–8.09 (m, 2H), 7.77 (s, 1H), 7.71 (s, 2H), 7.67 (s, 1H), 7.44 (s, 2H), 7.04–7.10 (m, 2H), 5.04 (s, 1H), 4.73–4.82 (m, 2H), 1.46 (d, J=6.5 Hz, 3H), and 1.44(d, J=7.7 Hz,3H).

Method BB

A 2000-mL round-bottomed flask equipped with a nitrogen inlet adapter and magnetic stir bar was charged with 11.3 g of 4-fluorophenylglyoxal hydrate from Method A, Step B, 42.8 g of (R)-1-(3,5-bis(trifluoromethyl)phenyl)-ethanol from Method A, Step A and 1000 mL of toluene. To this solution was added 1.26 g of p-toluenesulfonic acid at room temperature. The reaction mixture was heated to reflux under a Dean-Stark trap and after 72 h another aliquot of p-toluenesulfonic acid was added. (Note: Excessive amounts of p-TSA will cause decomposition of the product.) The reaction mixture was further heated a total of 137 h, cooled, and poured into 200 mL of saturated sodium bicarbonate solution. The phases were separated, and the aqueous phase was reextracted with ethyl acetate. The combined organic phases were washed with brine, dried over magnesium sulfate, filtered and concentrated. FC on 1500 g of silica gel (gradient elution with 20–75% methylene chloride/hexanes) afforded 23 g (53%) of title compound as a white solid after vacuum drying and 14.2 g (33%) of recovered starting alcohol. NMR spectra was same as for Method AA.

Step B: (2-R)-2-((R)-1-(3,5-Bis(trifluoromethyl)phenyl) ethoxy -2- (methoxycarbonylmethoxy)-4'-fluoroacetophenone(higher $R_f$ diastereomer) and (2-S)-2-((R)-1-(3,5-bis(trifluoromethyl)phenyl)-ethoxy)-2-(methoxycarbonylmethoxy)-4'- fluoroacetophenone (lower $R_F$ distereomer)

A 500-mL round-bottomed flask equipped with a nitrogen inlet adapter was charged with 4.38 g of 2,2-di-((R)-1-(3,5-bis(trifluoromethyl)phenyl)ethoxy)4'-fluoroacetophenone from Step A, Method BB and 2.5 mL of methylene chloride and cooled at 0° C. To this solution was added 0.74 mL of methyl sulfide followed by 0.85 mL of boron trifluoride diethyl etherate and the reaction mixture was allowed to warm to room temperature. After 18 h, 1.1 mL of methyl glycolate was added, and the reaction mixture was stirred at room temperature for 24 h. The resulting solution was diluted with methylene chloride and poured into 100 mL of saturated sodium bicarbonate. The phases were separated and the aqueous phase was extracted with two portions of methylene chloride. The combined organic phases were washed with brine, dried over magnesium sulfate, filtered and concentrated. The residue was purified by FC (gradient elution with 15–100% ether/hexanes or 0–15% methylene chloride/hexanes) to afford 1.63 (37%) of recovered starting material, 0.654 mg (20%) of the higher (2-R) title diastereomer, some mixed fractions, and 1.32 g of the lower (2-S) title diastereomer containing some of the (R) alcohol biproduct. The NMR of each was the same as in Method A.

Method C

A solution of 25 mg of 2,2-di-((R)-1-(3,5-bis (trifluoromethyl)phenyl)-ethoxy)4'-fluoroacetophenone, obtained as in Method B, Step A, and 2.2 mg of methyl glycolate in 2 mL of methylene chloride was cooled to 0° C. in an ice bath and 0.010 mL of trifluoromethanesulfonic acid was added. After 1 h, the reaction was quenched into a mixture of sodium bicarbonate solution and ether. Work-up and FC as in Method A, Step C afforded initial samples of the two title compounds. The NMR of each was the same as in Method A.

EXAMPLE 2

(2-R)-2-((R)-1-(3,5-Bis(trifluoromethyl)phenyl) ethoxy)-1-(carboxymethoxy)-4'-fluoroacetophenone (higher $R_f$ diastereomer)

To a solution of 100 mg of (2-R)-2-((R)-1-(3,5-bis (trifluoromethyl)-phenyl)ethoxy)-2-(methoxycarbonylmethoxy)4'-fluoroacetophenone (higher $R_f$ diastereomer) from Example 1 in 10 mL of methanol was added 2 mL of sat'd sodium bicarbonate solution. The reaction was stirred at room temperature for 16 h and then most of the methanol was removed in vacuo. The remaining mixture was diluted with water, acidified with 18% aqueous citric acid to pH=3 and extracted twice with ethyl acetate. The organic layers were each washed with brine, dried over sodium sulfate, combined and evaporated. FC of the residue (30% ethyl acetate/hexanes, then 1% acidic acid in 50% ethyl acetate/hexanes) gave after evaporation to dryness 85 mg of title compound. NMR (CDCl$_3$): δ1.55 (d, 3 H, J=6.5

Hz), 4.21 and 4.28 (ABq, 2 H, J=6.9 Hz), 5.18 (q, 1H, J=6.5 Hz), 5.25 (s, 1 H), 7.08 (m, 2 H), 7.75 (s, 2 H), 7.80 (s, 1 H), 8.00 (m, 2 H).

EXAMPLE 3

(2-R)-2-((R)-1-(3,5-Bis(trifluoromethyl)phenyl) ethoxy)-2-(carboxymethoxy)4'-fluoroacetophenone (higher $R_f$ diastereomer) and (2-S)-2-((R)-1-(3,5-bis (trifluoromethyl)phenyl)ethoxy)-2-(carboxymethoxy)4'-fluoroacetophenone (lower $R_f$ diastereomer)

A mixture of (2-R)- and (2-S)-2-((R)-1-(3,5-bis (trifluoromethyl)-phenyl)ethoxy)-2-(methoxycarbonylmethoxy)4'-fluoroacetophenone from Example 1, Method B, Step B was treated as in Example 2. The crude product was purified on Prep TLC (1% acidic acid in 50% ethyl acetate/hexanes) to easily separate clean higher $R_f$ (2-R) acid (identical to Example 2) and the lower $R_f$ (2-S) acid. NPR (CDCl$_3$): δ1.52 (d, 3 H, J=6.5 Hz), 4.20 (ABq, 2 H, J=17 Hz), 5.06 (q, 1H, J=6.5 Hz), 5.51 (s, 1H), 7.08 (m, 2 H), 7.72 (s, 3 H), 8.06 (m, 2 H).

EXAMPLE 4

(1-S,2-R)-2-((R)-1-(3,5-Bis(trifluoromethyl)phenyl) ethoxy)-2-(carboxymethoxy) 1-(hydroxy)-1-(4-fluorophenyl)ethane and (1R,2-R)-2-((R)-1-(3,5-bis (trifluoro-methyl)phenyl)ethoxy)-2-(carboxymethoxy)-1-(hydroxy)-1-(4-fluorophenyl)ethane (derived from the higher $R_f$ (2-R)-acid diastereomer from Example 2)
Method A:

To a solution of 75 mg of (2-R)-2-((R)-1-(3,5-bis (trifluoromethyl)-phenyl)ethoxy)-2-(carboxymethoxy)4'-fluoroacetophenone (higher $R_f$ diastereomer) from Example 2 in 4 mL of methanol was added 12 mg of sodium borohydride at room temperature. The reaction was stirred for 1 h and was then quenched with water, acidified with citric acid to pH=3, and extracted twice with ethyl acetate. The organic layers were each washed with brine, dried over sodium sulfate, combined and evaporated. HPLC on a reverse phase phenyl column (65% A: 35%B, A=10 mM ammonium acetate in water: B=7.2 mM ammonium acetate in 92.8% acetonitrile/7.2% methanol) of the residue indicated a 90:10 ratio of a faster ($R_t$=14 min): slower ($R_t$=17 min) diastereomer alcohol products. Prep HPLC separated the pure faster, major diastereomer which on collection, concentration in vacuo and lyophilization of the residual water afforded the (1-S) title product as the ammonium salt. The stereochemical assignment for the major isomer was made based on NMR comparison of the derived major lactone (see Example 6) and the 2 lactams (see Example 7).

(1-S,2R), Faster $R_t$, major product:
NMR (CD$_3$CN/trace TFA): δ1.41 (d, 3 H, J=6.5 Hz), 4.06 and 4.16 (ABq, 2 H, J=17 Hz), 4.46 (d, 1 H, J=6 Hz), 4.66 (d, 1 H, J=6 Hz), 5.07 (q, 1H, J=6.5 Hz), 7.01 (m, 2 H), 7.42 (m, 2 H), 7.79 (s, 2 H), 7.88 (s, 1H). Mass Spec (HPLC/MS, negative ion mode): 469 (M-1) (1-R,2-R), Slower $R_t$ title product: Mass Spec (HPLC/MS, negative ion mode): 469 (M-1)
Method B:

To a solution of 10 mg of (2-R)-2-((R)-1-(3,5-bis (trifluoromethyl)-phenyl)ethoxy)-2-(methoxycarbonylmethoxy)-4'-fluoroacetophenone (higher $R_f$ ester diastereomer) from Example 1 in 2 mL of methanol was added 1 mg of sodium borohydride at room temperature. The reaction was stirred for 1 h and was then quenched with sat'd sodium bicarbonate and stirred for 24 h at room temperature. HPLC on a reverse phase phenyl column (65% A: 35%B, A=10 mM ammonium acetate in water: B=7.2 mM ammonium acetate in 92.8% acetonitrile/7.2% methanol) of the reaction mixture indicated a reversed 10:90 ratio of the same faster slower diastereomeric alcohol products as seen in Method A.

EXAMPLE 5

(1R and/or 1S,2-S)-2-((R)-1-(3,5-Bis(trifluoromethyl) phenyl)ethoxy)-2-(carboxy-methoxy)-1-hydroxy-1-(4-fluorophenyl)ethane (from the lower $R_f$ acid diastereomer)

Using essentially the same procedure as in Example 4 but substituting the lower acid from Example 3, the title compound(s) was (were) prepared. NMR and HPLC analysis as in Example 4 only indicated a single product peak ($R_t$=20 min). Prep HPLC afforded a sample of the title compound(s).

NMR (CD$_3$CN/trace TFA): δ1.28 (d, 3 H, J=6.5 Hz), 3.77 and 3.87 (ABq, 2 H, J=16 Hz), 4.71 (d, 1 H, J=2 Hz), 4.79(q, 1H, J=6.5Hz), 4.86 (d, 1 H, J=2 Hz), 6.95 (m, 2 H), 7.42 (m, 2 H), 7.65 (s, 2 H), 7.78 (s, 1H). Mass Spec (HPLC/MS, negative ion mode): 469 (M-1)

EXAMPLE 6

(2-R ,3-S)-2-((R)-1-(3,5-Bis(trifluoromethyl)phenyl) ethoxy)-3-(4-fluorophenyl)-5-oxo-1,4-dioxane To a solution of 33 mg of pure, faster isomer from Example 4 in 2 mL of water was added 18% aqueous citric acid until pH 3. This was extracted twice with ethyl acetate and the organic layers were washed with brine, dried over sodium sulfate, combined and evaporated to give 25 mg of the free acid.

This was taken up in 5 mL of ether and 1 drop of acetic acid and 100 mg of 4A sieves were added. The mixture was stirred at room temperature for 3 days and concentrated in vacuo to dryness. The residue was triturated with hexanes and filtered and the filtrate was concentrated to give 15 mg of crude lactone. Rapid FC (25 to 30% ethyl acetate/ hexanes) afforded a pure sample of lactone. NMR assignment to the (3-S) stereochemistry was based on comparison to the known lactams (see Example 7).

NMR (CDCl$_3$): δ1.43 (d,3 H, J=6.5 Hz), 4.44 and 4.50 (ABq, 2 H, J=17 Hz), 4.59 (d, 1H, J=2 Hz), 4.91 (q, 1 H, J=6.5 Hz), 5.49 (d, 1 H, J=2 Hz), 7.08 (m, 2 H), 7.19 (s, 2 H), 7.40 (m, 2 H), 7.68 (s, 1H).

EXAMPLE 7

(2-R,3-R)-2-((R)-1-(3,5-Bis(trifluoromethyl)phenyl) ethoxy)-3-(4-fluorophenyl)-5-oxomorpholine (higher $R_f$ product) and (2-R,3-S)-2-((R)-1-(3,5-bis (trifluoromethyl)-phenyl)ethoxy)-3-(4fluorophenyl)-5-oxomorpholine (lower $R_f$ product)

To a solution of 20 mg of (2-R)-2-((R)-1-(3,5-bis (trifluoromethyl)-phenyl)ethoxy)-2-(methoxycarbonylmethoxy)4'-fluoroacetophenone (higher $R_f$ ester diastereomer) from Example 1 and 9.5 mg of ammonium acetate in 1 mL of isopropanol at room temperature was added 7.8 mg of sodium cyanoborohydride. The reaction was heated at 50° C. for 16 h at which time the reaction was cooled, quenched into water and extracted twice with ethyl acetate. The organic layers were each washed with brine, dried over sodium sulfate, combined and evaporated. Prep TLC (3% methanol in 60% ethyl acetate/ hexanes) gave separation of pure higher $R_f$, trans (3-R)-lactam product from the desired lower $R_f$, cis (3-S)-lactam product. HPLC on a reverse phase phenyl column (65% A:35%B, A=10 mM ammonium acetate in water: B=7.2 mM ammonium acetate in 92.8% acetonitrile/7.2% methanol) of the lower product indicated some faster eluting impurities. Thus, prep HPLC was used to afford the desired pure, (3-S)-lactam diastereomer.

Faster $R_f$, trans (3-R) title product:

NMR (CDCl$_3$): δ1.53 (d, 3 H, J=6.5 Hz), 4.24 and 4.39 (ABq, 2 H, J=17 Hz), 4.38 (d, 1 H, J=4 Hz), 4.56 (dd, 1 H, J=3 and 4 Hz), 4.95 (q, 1 H, J=6.5 Hz), 6.07 (br s, 1 H), 7.02 (m, 2 H), 7.19 (m, 2 H), 7.49 (s, 2 H), 7.74 (s, 1H).

Slower $R_f$, cis (3-S) title product:

NMR (CDCl$_3$): δ1.42 (d, 3 H, J=6.5 Hz), 4.25 and 4.31 (ABq, 2 H, J=17 Hz), 4.54 (dd, 1H, J=1 and 4 Hz), 4.75(d, 1 H, J=4 Hz), 4.87 (q, 1 H, J=6.5 Hz), 6.04 (brs, 1 H), 7.07 (m, 2 H), 7.09 (s, 2 H), 7.30 (m, 2 H), 7.66 (s, 1 H).

EXAMPLE 8

(1-R and 1-S ,2-R)-2-((R)-1-(3,5-Bis (trifluoromethyl)phenyl)ethoxy)-2-(2-hydroxyethoxy)-1-hydroxy-1-(4-fluorophenyl)ethane To a solution of 25 mg of (2-R)-2-((R)-1-(3,5-bis (trifluoromethyl)-phenyl)ethoxy)-2-(methoxycarbonylmethoxy)-4'-fluoroacetophenone (higher $R_f$ ester diastereomer) from Example 1 in 1 ml of methanol was added 4 mg of sodium borohydride at room temperature. The reaction was stirred for 16 h and was then quenched 18% aqueous citric acid. HPLC on a reverse phase phenyl column (gradient of 65% A: 35%B to 10% A: 90% B over 50 min, A=10 mM ammonium acetate in water: B=7.2 mM ammonium acetate in 92.8% acetonitrile/7.2% methanol) of the reaction mixture indicated a 4:1 ratio of diastereomeric diol products ($R_f$=23 and 24 min). The reaction was diluted with water and extracted twice with ethyl acetate. The organic layers were each washed with brine, dried over sodium sulfate, combined and evaporated. Prep TLC (60% ethyl acetate/hexanes) afforded 8 mg of title compound as a 4:1 mixture of diastereomers.

NMR (CDCl$_3$): δ1.38 and 1.49 (2 d, 3 H, J=6.5 Hz), 2.18 and 2.95 (2 br s, 2 H), 3.3 –4.0 (4 m, 4 H), 4.24 and 4.37 (2 d, 1 H, J=4.5 and 7.5 Hz), 4.66 and 4.69 (2 d, 1 H, J=4.5 and 7.5 Hz), 4.80 and 4.96 (2 q, 1 H, J=6.5 Hz), 6.8–7.1 (m, 2 H), 7.2–7.35 (m, 2 H), 7.20 and 7.65 (2 s, 2 H), 7.66 and 7.77 (2 s, 1 H).

EXAMPLE 9

(2-R,3-R and 3-S)-2-((R)-1-(3,5-Bis (trifluoromethyl)phenyl)ethoxy)-3-hydroxy-3-(4-fluorophenyl)-5-oxomorpholine To a solution of 75 mg of (2-R)-2-((R)-1-(3,5-bis (trifluoromethyl)-phenyl)ethoxy)-2-(methoxycarbonylmethoxy)-4'-fluoroacetophenone (higher $R_f$ ester diastereomer) from Example 1 in 4 mL of isopropanol was added 120 mg of ammonium acetate at room temperature. The reaction was heated at 50° C. for 40 h and was then evaporated. HPLC on a reverse phase phenyl column (gradient of 65% A:35%B to 10% A: 90% B over 50 min, A=10 mM ammonium acetate in water: B=7.2 mM ammonium acetate in 92.8% acetonitrile/7.2% methanol) of the reaction mixture indicated numerous products with the $R_f$ of the desire product at 21.9 min). Prep TLC (60% ethyl acetate/hexanes) afforded several bands which were isolated and analyzed by HPLC. The fraction most enriched in the desired (3-S) product at $R_f$=21.9 was used to collect 4 mg of purified title compound which was confirmed by NMR. Equilibration in water or acetonitrile for several days afforded a 3–4 to 1 mixture of (3-S) ($R_t$=21.9 min) to (3-R) ($R_t$=21.4) title compounds. (3-S) NMR (CD$_3$CN): δ1.38 (d, 3 H, J=6.5 Hz), 4.19 and 4.25 (ABq, 2 H, J=17 Hz), 4.37 (s, 1 H), 4.63 (br s, 1 H), 4.90 (q, 1 H, J=6.5 Hz), 7.05 (m, 2 H), ), 7.18 (br s, 1 H), 7.28 (s, 2 H), 7.47 (m, 2 H), 7.78 (s, 1 H). (3-R) NMR (CD$_3$CN): δ1.42 (d, 3 H, J=6.5 Hz), 4.19 and 4.29 (ABq, 2 H, J=17 Hz), 4.46 (s, 1 H), 4.65 (br s, 1 H), 5.06 (q, 1 H, J=6.5 Hz), 6.95 (m, 2 H), ), 7.18 (br s, 1 H), 7.39 (m, 2 H), 7.75 (s, 2 H), 7.88 (s, 1 H).

EXAMPLE 10

N-((1,4-Dihyro-1,2,4-triazol-5-on-3-yl)methyl)-(S)-(4-fluorophenyl)gylcine TFA salt Step A: N-Benzyl-N-((1,4-dihyro-1,2,4-triazol-5-on-3-yl) methyl)-(S)-(4-fluorophenyl)gylcine TFA salt To a solution of 145 mg of N-benzyl-(S)-(4-fluorophenyl)gylcine sodium salt in 10 mL of acetonitrile was added 0.10 mL of DIPEA and 25 mg of 3-(chloromethyl)-1,4-dihyro-1,2,4-triazol-5-one. The reaction was stirred at room temperature for 20 h and then concentrated. The residue was dissolved in 10 mL of water containing some TFA and the title product was isolated by repeatative Prep HPLC (gradient of 90% A: 10%B to 65% A: 35% B over 18 min, A=10 mM ammonium acetate in water: B=7.2 mM ammonium acetate in 92.8% acetonitrile/7.2% methanol) to give 106 mg as a white solid. Mass Spec (HPLC/MS): 357(M-1)

Step B: N-((1,4-Dihyro-1,2,4-triazol-5-on-3-yl)methyl)(S)-(4-fluorophenyl)gylcine TFA salt A solution of 100 mg of N-benyl-N-((1,4-dihyro-1,2,4-triazol-5-on-3-yl)methyl)-(S)-(4-fluorophenyl)gylcine from Step A in 3 mL of methanol was hydrogenated on a Parr shaker for 16 h at 50 psi with 20 mg of 20% Pd(OH)$_2$ on carbon (50% by wt water). The percipitated product was dissolved by addition of water and TFA. The catalyst was removed by filtration and the filtrate was concentrated to 3 mL and lyophilized. The residue was triturated with 1 mL of water and re-lyophylized to afford 47 mg of the title product as a white solid. Mass Spec (HPLC/MS): 357(M-1)

NMR (D$_2$O): δ4.16 (Abq, 2 H, J=9.4 Hz), 5.19 (s, 1 H), 7.24 (t, 2 H, J ×8.8 Hz), 7.47 (m, 2 H).

EXAMPLE 11

N-((1,4-Dihyro-1,2,4-triazol-5-on-3-yl)methyl)-(S)-(4-fluorophenyl)gyicinol TFA salt Step A: N-Benyl-(S)-(4-fluorophenyl)gylcinol To a solution of 280 mg of N-benzyl-(S)-(4-fluorophenyl)gylcine sodium salt in 10 mL of TIF was added 0.06 mL of acetic acid and 3.0 mL of 2M borane-dimethylsulfide in THF. The reaction was stirred at room temperature for 16 h and was then quenched with methanol. The mixture was diluted with water and aq. sodium carbonate and extracted 3× with methylene chloride. The organic layers were washed with brine, dried over sodium sulfate and evaporated. FC (10% methanol in methylene chloride) afforded 190 mg of title compound. Mass Spec (HPLC/MS): 246 (M-1)

Step B: N-Benyl-N-((1,4dihyro-1,2,4-triazol-5-on-3-yl) methyl)-(S)-(4-fluorophenyl)gylcinol To a solution of 180 mg of N-benzyl-(S)-(4-fluorophenyl) gylcinol in 5 mL of acetonitrile was added 0.39 mL of DIPEA and 60 mg of 3-(chloromethyl)-1,4-dihyro-1,2,4-triazol-5-one. The reaction was stirred at room temperature for 16 h and then at 50° C. for 30 h and then concentrated.

The residue was dissolved in 10 mL of water containing some sodium hydroxide and extracted with methylene chloride. HPLC/MS indicated that the product was in the aqueous layer. This was adjusted to pH 8 and extracted 3x with methylene chloride. The organic layers were washed with brine, dried over sodium sulfate and evaporated to give 90 mg of title product. Mass Spec (HPLC/MS): 343 (M-1)

Step C: N-((1,4-Dihyro-1,2,4-triazol-5-on-3-yl)methyl)-(S)-(4-fluorophenyl)gylcine TFA salt A solution of 80 mg of N-benyl-N-((1,4-dihyro-1,2,4-triazol-5-on-3-yl)methyl)-(S)-(4-fluorophenyl)gylcinol from Step B in 5 ML of methanol was hydrogenated on a Parr shaker for 6 h at 50 psi with 30 mg of 20% $Pd(OH)_2$ on carbon (50% by wt water). The percipitated product was dissolved by addition of water and TFA. The catalyst was removed by filtration and the filtrate was concentrated. The residue was taken up in 2 mL of methanol and loaded onto a 500 mg Varian SCX resin cartridge. The resin was washed 3x5 mL with methanol (no product by HPLC/MS) and was then eluted with 3x5 mL of 2M ammonia in methanol. HPLC/MS indicated the clean product in the first two elutions. These were concentrated and 3x methylene chloride evaporated. The residue was taken up in methylene chloride, TFA was added and the solution was evaporated to dryness. Mass Spec (HPLC/MS): 253 (M-1)

GENERAL PROCEDURES FOR METABOLISM STUDIES

The mammalian metabolites of 2-(R)-(1-(R)-(3,5-bis (trifluoromethyl)-phenyl)ethoxy)-3-(S)-(4-fluoro)-phenyl-4-(3-(5-oxo-1H,4H-1,2,4-triazolo)methyl-morpholine were obtained and identified by administration of the parent compound to mammalian species or by incubation of the parent compound with liver microsomes essentially as described herein.

Hepatocytes were harvested from male Sprague-Dawley rat livers or human livers and cultured on a matrigel support and treated with 0.1 μM dexamethasone or 50 μM rifampicin, respectively, for 48 hr prior to the addition of the test compounds. A 2.5 mM stock solution of [$^{14}$C]2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo) methylmorpholine, [$^{14}$C]M-1 or [$^{14}$C]M-2 in DMSO was added to the plates such that the final concentration of test compound was 25 μM and DMSO was 1% (v/v). The cultures were incubated for 4, 6 or 24 hr for rat hepatocytes and 48 hr for human hepatocytes. The incubation mixtures (500 μL) contained 10 μM of test compound, 100 mM phosphate buffer pH 7.4, NADPH-regenerating system, microsomes containing expressed CYP isoforms (CYP1A2, CYP2A6, CYP2B6, CYP2C8, CYP2C9, CYP2C19, CYP2D6, CYP2E1 or CYP3A4) and cytochrome P-450 reductase. The reactions were initiated by adding NADP and proceeded at 37° C. for 15–45 min. Acetonitrile extracts from microsomal and hepatocyte incubates were dissolved in 50% aqueous methanol and fractionated by HPLC. The separation was accomplished on a Zorbax RX C8 analytical column (5 μm, 4.6x250 mm). The mobile phase consisted of solvent A (10 mM ammonium acetate in water) and solvent B (7.3 mM ammonium acetate in 92.7% acetonitrile and 7.3% methanol. The column was eluted by a linear gradient from 35 to 80% B over 40 min at a flow rate of 1 mL/min. Fractions of major metabolites were subjected to LC-MS/MS analysis. Further purification was done using isocratic conditions prior to NMR analysis.

Preparation of Liver Microsomes

All liver microsomal and cytosolic fractions were prepared using the following procedure. Thawed livers were homogenized with 2 volumes of 50 mM Tris-buffer (pH 7.5) containing 1.15% KCl. For microsomal and cytosolic preparations, the homogenate was centrifuged for 20 min at 9,000xg and the resulting supernatant was centrifuged for 60 min at 105,000xg. The resulting cytosolic fractions were re-centrifuged at 105,000xg for 60 min. Fractions of cytosol were aliquoted into small tubes and stored at −70° C. Subsequently, the microsomal pellets were washed with 10 mM EDTA containing 1.15% KCl and were centrifuged at 105,000xg for 60 min. Washed microsomes were resuspended in 10 mM potassium phosphate buffer (pH 7.4) containing 250 mM sucrose, aliquoted into small tubes, and stored at −70° C. Protein concentrations were determined by a modified Lowry assay (Smith et al., 1985). The specific cytochrome P450 content in each microsomal preparation was measured as described by Omura and Sato, *J. Biol. Chem.* 239, 2370–2378 (1964).

Oxidative Metabolism in Liver Microsomes or Expressed Recombinant CYP450 Isozymes The incubation mixtures (500 μL) contained 10 or 25 μM of test compounds, 100 mM phosphate buffer pH 7.4, NADPH-regenerating system (5 mM glucose-6-phosphate, 1 mM NADP and 0.7 I.U/mL glucose 6-phosphate dehydrogenase), 0.5 to 2 mg/mL liver microsomal protein prepared from rats and humans or microsomes from Baculovirus-infected sf21 cells containing 20 to 200 pmol expressed CYP isoforms (CYP1A2, CYP2A6, CYP2B6, CYP2C8, CYP2C9, CYP2C19, CYP2D6, CYP2E1 or CYP3A4) and cytochrome P450 reductase. Stock solutions of the substrates in methanol were made such that final concentration of methanol in the reaction mixture was 3%. The reactions were initiated by adding 50 μL of 10 mM NADP and proceeded at 37° C. for 15–45 min. After incubation, the reactions were terminated by the addition of four volumes of acetonitrile. The suspensions were mixed vigorously and centrifuged at 3000xg for 5 min. The supernatants were dried and redissolved in 50% methanol for HPLC analysis using method A described below.

Glucuronidation in Liver Microsomes

The typical reaction mixture (500 μl) containing 10 mM $MgCl_2$, 2% glycerol, 0.02% lubrol PX, 3 mM UDPGA, 1 mg liver microsomes, 50 mM bis-tris propane buffer (pH 8.5) and ~10 or 25 μM compound (in 15 μl methanol) was incubated at 37° C. for 30–60 min. After incubation, the reactions were terminated by the addition of four volumes of acetonitrile and processed and analyzed by HPLC as mentioned above.

Metabolism in Primary Cultures of Rat and Human Hepatocytes

Hepatocytes were harvested from male Sprague-Dawley rats and cultured on a matrigel support and treated with 0.1 μM dexamethasone to maintain the activities of CYP isozymes for 48 hr prior to the addition of the substrate (Pang et al., *Toxicol Appl Pharmacol*, 142, 87–94, 1997). Hepatocytes cultures were prepared from human livers and subsequently treated with 50 uM rifampicin for 48 hr prior to the addition of the substrate (Li et al., *J Tiss Cult Meth*, 14, 139–146, 1992). The cultures (prepared on 60 mm Petri dishes) were kept with 3 mL of Williams Medium at 37° C. A 2.5 mM stock solution of [$^{14}$C]2-(R)-(1-(R)-(3,5-bis (trifluoro-methyl) -phenyl)ethoxy)-3-(S)-(4-fluoro)phenyl-4-(3-(5-oxo-1H,4H-1,2,4-triazol -methylmorpholine, [$^{14}$C] M-1 or [$^{14}$C]M-2 in DMSO was added to the plates such that the final concentration of test compound was 25 μM and DMSO was 1%. The cultures were incubated for 4, 6 or 24 hr for rat hepatocytes and 48 hr for human hepatocytes. Following incubation, the plates were scraped and the cell suspensions were transferred to test tubes. The plates were further washed with 3 mL methanol and the wash was mixed with the cell suspensions. The samples were sonicated for 10 min at room temperature and centrifuged for 10 min at 3000×g. The supernatants were then transferred to clean tubes and dried. The samples were redissolved in water for HPLC analysis using method A.

Metabolite Purification

Acetonitrile extracts from microsomal and hepatocytes incubates were redissolved in 50% methanol and fractionated according to HPLC method A. Fractions of major metabolites were subjected to LC-MS/MS analysis. Further purification was done using isocratic conditions (system B or C) prior to NMR analysis.

HPLC Analysis

Method A was conducted on a Shimadzu HPLC system (Shimadzu Scientific Instruments Inc., Columbia Md.). The parent compounds and their metabolites were monitored directly using a radiometric detector (INUS Systems Inc. Tampa, Fla.) and Ultima-Flow M (Packard Instrument Co., Meridan Conn.) as scintillant at a flow rate of 3 mL/min. The separation was accomplished on a Zorbax RX C8 analytical column (5 um, 4.6×250 mm). The mobile phase consisted of solvent A (10 mM ammonium acetate in water) and solvent B (7.3 mM ammonium acetate in 92.7% acetonitrile and 7.3% methanol). Samples were injected via the autosampler and the column was eluted by a linear gradient from 35 to 80% B over 40 min at a flow rate of 1 mL/min. The HPLC elution time using method A for MK-0869 was 28 min. Methods B and C were developed for the purification of metabolites for NMR analysis. The separation was accomplished on a Zorbax ODS analytical column (5 um 4.6×250 mm) using the instrument described above. Samples were injected via the autosampler and the column was eluted isocratically with 40%B (method B) or 50%B (method C). The eluent was collected in 1 mL fractions using a Shimadzu fraction collector. An aliquot from each fraction was counted directly in a liquid scintillation counter (Beckman Instruments, Fullerton, Calif.) using ScintiSafe (Fisher Scientific Inc., Pittsburgh, Pa.) as scintillant to monitor the presence of parent-related material.

LC/MS/MS Analysis

Full scan mass spectra and product ion mass spectra of metabolites were obtained on a tandem mass spectrometer (SCIEX API III) using the ion spray interface. For collision-induced dissociation experiments (MS/MS), the collision gas was argon. Positive and negative ion detection was used. All on-line analyses were done using the HPLC conditions described for method A. The column effluent was split such that 5% entered the ionspray interface. Prior to NMR analysis, slug injections of purified samples were done to confirm molecular weight and purity using electrospray ionization in the positive ion mode. Purified metabolites were analyzed by proton NMR on a 500 MHz Varian instrument using deuterated methanol or acetonitrile as solvent.

In Vitro Oxidative Metabolism in Liver Microsomes From Rats and Humans

Metabolite M-1

[$^{14}$C]2-(R)(1-(R)-(3,5-bis(trifluoromethyl)phenyl) ethoxy)-3-(S)-(4-fluoro)-phenyl-4-(3-(5-oxo-1H,4H-1,2,4-triazolo)methylmorpholine was metabolized in microsomes from rat and human livers in the presence of an NADPH regenerating system (<2% conversion in 45 min in both microsomal preparations) and the major metabolite (M-1) was identified to be the N-dealkylated derivative. By ion-spray mass spectrometry, a molecular ion [M+H]$^+$ of 438 was observed indicating the loss of triazolone methyl group of the parent compound ([M+H]$^+$=535).

Metabolite M-2

M-1 was readily metabolized in rat and human liver microsomes such that only ~50% parent compound remained after 15 min incubation. The major product, designated as M-2, eluting at 38 min in HPLC method A, was less polar than M-1 and was identified as an imine derivative. Based on LC-MS analysis, a molecular ion [M+H]$^+$ of 436 was observed indicating the loss of two mass unit from M-1 ([M+H]$^+$=438). NMR analysis confirmed the structure of M-2.

In Vitro Glucuronidation in Liver Microsomes From Rats and Humans

When 2-(R)-(1-(R)-(3,5-bis(trifluoromethyl)phenyl) ethoxy)-3-(S)-(4-fluoro)-phenyl-4-(3-(5-oxo-1H,4H-1,2,4-triazolo)methylmorpholine was incubated in liver microsomes from rats and humans, the formation of glucuronide of 2-(R)-(1-(R)-(3,5-bis(trifluoromethyl)phenyl) ethoxy)-3-(S)-(4-fluoro)-phenyl-4-(3-(5-oxo-1H,4H-1,2,4-triazolo)methylmorpholine was confirmed by LC-MS/MS. Similarly, a product was generated (~20% conversion in liver microsomes at 37° C. for 60 min) and confirmed by LC-MS/MS as the corresponding glucuronide when M-1 was incubated with liver microsomes from rats and humans in the presence of UDPGA.

Metabolic Profiles in Primary Cultures of Rat Hepatocytes

[$^{14}$C]M-1 was extensively metabolized in rat hepatocyte cultures after 6 hr with three major metabolites eluting at 27, 29 and 39 min in HPLC system (method A), designated as M4, M-3 and M-2, respectively. M-2 was confirmed by LC-MS/MS as the imine derivative of M-1, as described above. After incubation for 24 hr, the concentrations of M-3 declined with the concomitant increase of M4. These results suggest that M-3 may be precursors of M4. Additionally, the concentrations of several radioactive components eluting at 4, 9, 13 and 15 min also increased with time and the components eluting at 13, 15 were designated as M-6 and M-5. The major metabolites, including M-3 to M-6 were isolated for NMR analysis using HPLC methods A, B and C sequentially.

Metabolite M-3

The metabolite M-3 was assigned as a lactam derivative of M-1. From LC-MS analysis, the increase of 14 mass unit (m/z=452) was observed in the extracted ion chromatogram compared to the parent compound (m/z=438). The proposed structure was confirmed by $^1$H NMR analysis to match the metabolite isolated from hepatocyte culture.

Metabolite M-4

The metabolite M-4 was characterized as a 9:1 mixture of two hydroxylactam epimers, which were isolated from rat brain and plasma as two entities, assigned as M4-a and M4-b.

Metabolite M-5 and M-6

The metabolite M-6 was isolated from 24 hr incubations by consecutive chromatography using methods A and B. The precursor to the hydroxy acid M-6, namely M-5 as the keto acid derivative was present in incubates.

Metabolic Profiles in Primary Cultures of Human Hepatocytes

In cultured human hepatocytes, biotransformations of M-1 similar to those described above for the rat were observed although M4 appeared to be a very minor product.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

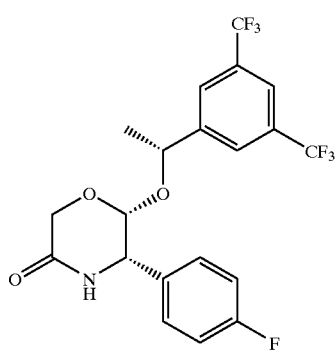

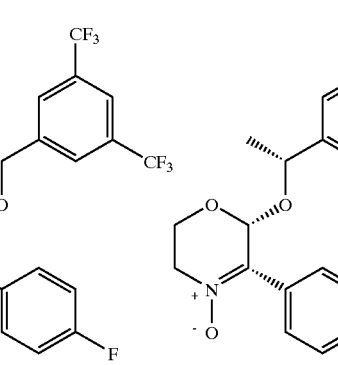

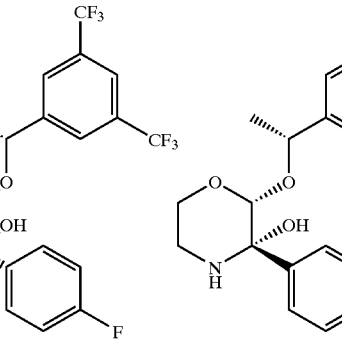

-continued

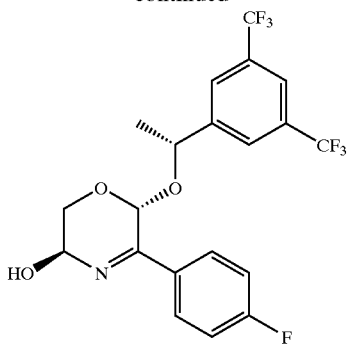

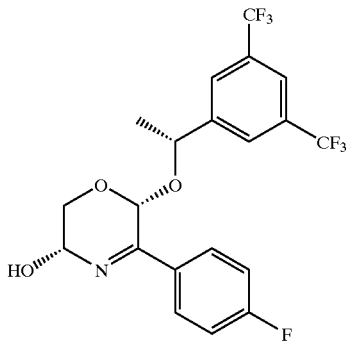

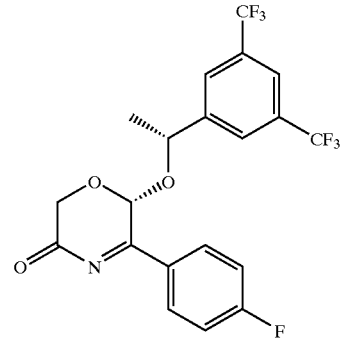

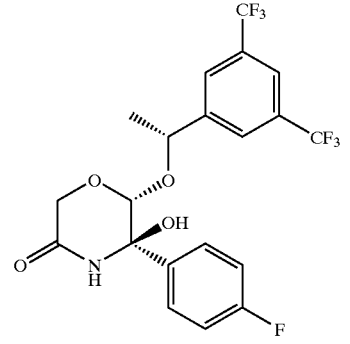

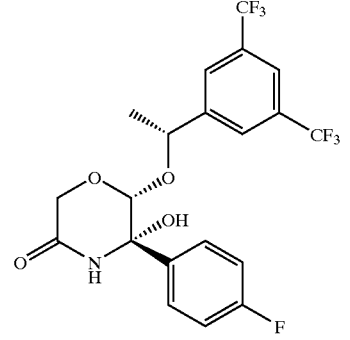

-continued

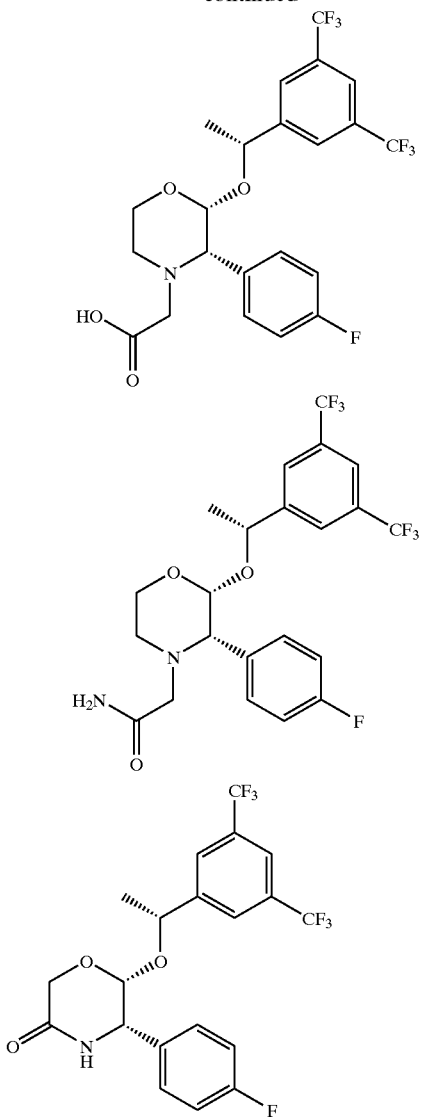

-continued

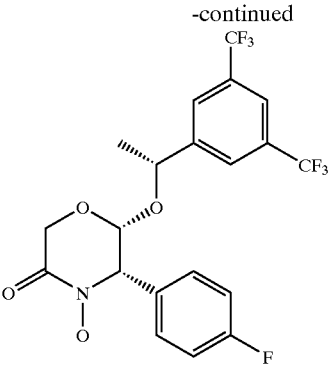

and pharmaceutically acceptable salts and individual diasteromers thereof in pure or partially purified form.

2. A pharmaceutical composition comprising a pharmaceutically acceptable carrier and the compound of claim 1.

3. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site in the mammal.

4. A method for the treatment of depression in a mammal in need thereof which comprises the administration to the mammmal of an effective amount of the compound of claim 1.

5. A method for the treatment of anxiety in a mammal in need thereof which comprises the administration to the mammmal of an effective amount of the compound of claim 1.

6. A method for the treatment or prevention of emesis in a mammal in need thereof which comprises the administration to the mammal of an effective amount of the compound of claim 1.

* * * * *